United States Patent [19]

Aldridge et al.

[11] 4,072,573

[45] Feb. 7, 1978

[54] PSEUDOMONAS AERUGINOSA BROTH

[75] Inventors: Clifton Aldridge, Maryland Heights; Sandra F. Gibson, Chesterfield; Gregory D. Rodgers, Florissant, all of Mo.

[73] Assignee: McDonnell Douglas Corporation, St. Louis, Mo.

[21] Appl. No.: 682,653

[22] Filed: May 3, 1976

[51] Int. Cl.$^2$ ............................................. C12K 1/06
[52] U.S. Cl. ................................................... 195/100
[58] Field of Search ................. 195/100, 103.5 R, 99, 195/101, 102, 103

[56] References Cited
PUBLICATIONS

W. Robert Bailey and Elvyn Scott, Diagnostic Microbiology, 2nd Ed., The C.V. Mosby Company; pp. 26, 147–148, 295–296; 1966.

Primary Examiner—Lionel M. Shapiro
Assistant Examiner—Robert J. Warden
Attorney, Agent, or Firm—Gravely, Lieder & Woodruff

[57] ABSTRACT

A broth medium for the detection of Pseudomonas aeruginosa in urine. The medium employs cetyl trimethylammonium bromide to inhibit growth of unwanted organisms that normally give positive results in tests for P. aeruginosa.

12 Claims, No Drawings

PSEUDOMONAS AERUGINOSA BROTH

BACKGROUND OF THE INVENTION

*Pseudomonas aeruginosa* (*P. aeruginosa*) is a microorganism which occurs in urine, wounds, ulcers, etc. The presence of this organism in urine is a reliable indicator of an infection in the urinary tract.

Pseudomonas is a gram-negative bacterium and is commonly a saprophyte but is also an opportunistic pathogen able to establish infection and to invade when the natural resistance of an individual is severely lowered. The organism has a higher growth temperature range (41° to 42° C) than saprophytic pseudomonas (20° to 30° C) and frequently causes hospital infections associated with middle ear or urinary tract infections and wounds or ulcers that have not healed promptly. It is frequently found in patients with severe burns. The organism is naturally resistant to several antibiotics commonly used, and thus chemotherapy is very difficult.

Some outbreaks of diarrhea in adults and especially among newborn children are said to be caused by this organism.

The medium of this invention is an improved medium designed for use with the optical detection system disclosed in U.S. applications Ser. Nos. 255,533 filed May 22, 1972 now abandoned and 461,249 filed Apr. 16, 1974 now U.S. Pat. No. 3,963,355 and in the improved devices disclosed and claimed in applications filed on even date herewith by Charles, Jones, Staples, and Wiegner entitled AUTOMATED MICROBIAL ANALYZER and MACHINE AND PROCESS FOR READING CARDS CONTAINING MEDICAL SPECIMENS. These applications describe mechanism and apparatus suitable for analyzing specimens for specific microorganisms using a plastic tray or card which contains a series of dried culture media contained in separate but connectable cells, each of the media being specific to a single organism. When the sample is inserted into the card, mixed with the media in the cells, and incubated in the machine; the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic activity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

We have discovered a medium which can selectively identify Pseudomonas aeruginosa organism in urine. Our medium can be used in the system developed in the aforementioned copending application entitled AUTOMATED MICROBIAL ANALYZER.

The medium is freeze dried in a well in the media card of said application AUTOMATED MICROBIAL ANALYZER and when a specimen is mixed with the medium in the well, positive results are indicated by means of a change in turbidity and pigment of the medium. The entire test can be completed within 12-18 hours, whereas current methods of detection require from 36 to 48 hours.

SUMMARY OF THE INVENTION

This invention involves a broth medium for the detection of *Pseudomonas aeruginosa* in urine.

The medium contains Trypticase soy broth, sodium nitrate, and cetyl trimethylammonium bromide.

The novelty of the invention lies in the use of cetyl trimethylammonium bromide, which operates to inhibit the growth of other gram-positive and gram-negative microorganisms which normally give positive results in tests for *Pseudomonas aeruginosa*, and in the addition of sodium nitrate so that the medium is functional in the low $O_2$ environment of the card used in the system of application entitled AUTOMATED MICROBIAL ANALYZER. It also is important that the medium be formulated at about 70° C.

DETAILED DESCRIPTION

The detection broth of the present invention contains from 2.7 to 3.3% (by weight) nutrients which are Trypticase Soy Broth from BBL, about 0.029 to about 0.031% cetyl trimethylammonium bromide which operates as a biological inhibitor to inhibit the growth of gram-negative organisms, and about 0.45 to about 0.55% (by weight) sodium nitrate which operates to stimulate growth of *P. aeruginosa* organism in a reduced oxygen environment.

The nutrient portion of the medium contains from about 27 gm to about 33 gm Trypticase soy broth per liter of broth medium. Trypticase Soy Broth is a mixture of peptones and contains per liter of distilled water, 17 grams of peptone derived from casein by pancreatic digestion, 3 grams of a papaic digest of soya meal high in vitamins, especially thiamine, 5 grams NaCl, 2.5 grams dipotassium phosphate, and 2.5 grams dextrose. It has a pH of about 7.3. Suitable substitutes for Trypticase soy broth are protease Peptone #3 (from DIFCO), and Thiotone (from BBL). (Any peptone containing sufficient vitamins will operate in this invention).

The purpose of the soy broth is to promote growth of *P. aeruginosa* organism.

A suitable base or acid is used to adjust the pH of the medium to 6.7 to 6.9.

An important aspect of this invention lies in the action of the chemical inhibitor, cetyl trimethylammonium bromide. This inhibitor acts to inhibit the growth of gram-negative organisms.

The concentration of cetyl trimethylammonium bromide can be from about 0.29 gm/l to about 0.31 gm/l and it is most effective at 0.3 gm/l. If the concentration is too high, a lower yield of positives occurs.

From about 4.75 gm/l to about 5.25 gm/l of an ingredient which helps growth of Pseudomonas and pigment production is incorporated into the medium to compensate for the shortage of $O_2$ in the wells of the plastic card used with application entitled AUTOMATED MICROBIAL ANALYZER. The additive is a nitrate salt, such as sodium nitrate.

Since the environment is low $O_2$, addition of $NaNO_3$ provides an electron acceptor so that highly aerobic pseudomonads can grow and produce pigment. The production of pigment of *Pseudomonas aeruginosa* and production of visible bio mass is the combination indicator.

The pigment of *Pseudomonas aeruginosa* referred to is a blue-green pigment which absorbs red light and is noticed, along with the increase in bio mass, by the mechanism described in application AUTOMATED MICROBIAL ANALYZER. The light transmitting characteristics of the medium are changed by the color change and the bio mass production.

EXAMPLE I

Preparation of 2X Broth for Use in Card Wells of System of AUTOMATED MICROBIAL ANALYZER

*Pseudomonas aeruginosa* detection broth is prepared by the following procedure:

Six grams of Trypticase Soy Broth, 1 gram of sodium nitrate and 0.06 grams of cetyl trimethylammonium bromide are mixed with 100 ml of distilled water. This composition is stirred for about five minutes and brought to a boil to insure all ingredients are in solution. The composition is adjusted to pH 6.8 at 70° C., which is an important step in maintaining the stability of the solution. The solution is returned to 100 ml and filter sterilized. It is placed in a well of the card described in application entitled AUTOMATED MICROBIAL ANALYZER and freeze dried before use.

Presence of *Pseudomonas aeruginosa* in the well is indicated by the formation of a blue-green pigment in the well caused by action of the organism on the medium as well as by an increase in the bio-mass in the medium resulting from growth of *P. aeruginosa*.

What is claimed is:

1. A broth medium for detection of *Pseudomonas aeruginosa* comprising:
   a. a nutrient source,
   b. a nitrate salt to assist in growth of Pseudomonas and pigment production in the condition of limited $O_2$, and
   c. cetyl trimethylammonium bromide to inhibit gram-negative organisms.

2. The medium of claim 1 which contains a detectible pigment in the presence of *Pseudomonas aeruginosa*.

3. The medium of claim 1 which contains a visible bio mass in the presence of *Pseudomonas aeroginosa*.

4. The medium of claim 1 wherein the nitrate salt is sodium nitrate.

5. The medium of claim 4 wherein in a 1X dilution about 4.75 gm/l to about 5.25 gm/l sodium nitrate is used.

6. The medium of claim 1 wherein in a 1X dilution about 27 gm/l to about 33 gm/l nutrient source is used.

7. The medium of claim 6 wherein the nutrient source is Trypticase Soy Broth.

8. The medium of claim 1 wherein in a 1X dilution the lack of $O_2$ is compensated by the addition of sodium nitrate, and the nutrient source is Trypticase Soy Broth.

9. The medium of claim 8 wherein about 4.75 to about 5.25 gm/l sodium nitrate is used, from about 0.29 to about 0.31 gm/l cetyl trimethylammonium bromide is used, and from about 27 to about 33 gm/l nutrient is used.

10. The medium of claim 1 wherein the pH is about 6.8.

11. A broth medium for detection of *Pseudomonas aeruginosa* comprising:
    a. a nutrient source,
    b. an additive to assist in growth of Pseudomonas and pigment production in the condition of limited $O_2$, and
    c. cetyl trimethylammonium bromide as a gram-negative organism inhibitor.

12. The medium of claim 11 wherein in a 1X dilution about 0.29 gm/l to about 0.31 gm/l cetyl trimethylammonium bromide is used.

* * * * *